(12) United States Patent
Peterson

(10) Patent No.: US 7,648,108 B2
(45) Date of Patent: Jan. 19, 2010

(54) PEDICURE PEDESTAL

(76) Inventor: Jeanette Peterson, 6904 N. Gunlock Ave., Tampa, FL (US) 33614

( * ) Notice: Subject to any disclaimer, the term of this patent is extended or adjusted under 35 U.S.C. 154(b) by 285 days.

(21) Appl. No.: 11/756,641

(22) Filed: Jun. 1, 2007

(65) Prior Publication Data
US 2008/0296447 A1 Dec. 4, 2008

(51) Int. Cl.
*F16M 11/38* (2006.01)
*A45D 29/00* (2006.01)
*A45D 29/20* (2006.01)
*E04G 1/00* (2006.01)

(52) U.S. Cl. .................. 248/166; 248/170; 248/168; 132/73; 132/75; 182/129

(58) Field of Classification Search ............. 248/166; 297/423.14, 423.18, 423.26, 423.29, 423.3, 297/423.39, 423.21, 423.2, 423.19, 188.1; 211/132.1, 124, 125, 126, 23, 26, 159; 36/58.5
See application file for complete search history.

(56) References Cited

U.S. PATENT DOCUMENTS

| | | | | |
|---|---|---|---|---|
| 1,947,758 A * | 2/1934 | Cousins | ................... | 312/235.5 |
| 2,519,677 A * | 8/1950 | MacKay | ..................... | 33/3 B |
| 4,258,827 A * | 3/1981 | Klose | ...................... | 182/33.3 |
| 6,012,548 A * | 1/2000 | Kim | .......................... | 182/165 |
| D433,722 S * | 11/2000 | Capoano et al. | .............. | D28/61 |
| D433,772 S * | 11/2000 | Capoano | ..................... | D28/61 |
| 6,532,969 B2 * | 3/2003 | Nuzzo | ....................... | 132/286 |
| 6,832,688 B1 * | 12/2004 | Rivera et al. | ................ | 206/581 |
| 2005/0284701 A1 * | 12/2005 | Gibson et al. | ............... | 182/165 |
| 2005/0285489 A1 * | 12/2005 | Brother | ................... | 312/235.5 |

* cited by examiner

*Primary Examiner*—J. Allen Shriver, II
*Assistant Examiner*—Christopher Garft
(74) *Attorney, Agent, or Firm*—Dennis G. LaPointe

(57) ABSTRACT

A pedicure pedestal assembly is formed as a foldable frame. A foot support member is located between the legs of a U-shaped frame member and attached thereto at an intermediate location thereof. A pivotable frame member is pivotably attached to the U-shaped frame member at a location above the foot support member so as to form the free-standing foldable pedestal frame assembly when in an open position. A work station platform is pivotably attached on each side to the legs between the foot support member and the pivotable frame attachment. The work station platform has spaced-apart parallel notches for adjustable engagement with a transverse member attached to the pivotable frame member, such that when the pedestal frame assembly is opened, the work station platform is oriented in a horizontal orientation. The foot support has a heel rest portion and a height adjustable toe rest member.

15 Claims, 11 Drawing Sheets

PEDICURE PEDESTAL

FIELD OF INVENTION

The invention relates to the field of pedicures, more specifically, to a pedestal for use in doing a pedicure for one self or another person.

BACKGROUND OF THE INVENTION

The invention herein recognized a need to develop a foot rest to provide a steady platform that makes a person's foot readily accessible for a do-it-yourself pedicure, as well as making a working station that provides easy access to tools and supplies, all in one device.

SUMMARY OF THE INVENTION

The invention is a pedicure pedestal that provides for a steady platform that makes a person's foot readily available for a do-it-yourself pedicure. It provides for a foot rest angle that is adjustable to accommodate different user's levels of flexibility. This is done using spaced-apart notches under the work station platform or tray that engages a transverse rod or member on part of the frame system.

The toe rest adjusts up or down the foot rest of different size feet. Set pins are preferably used to position the toe rest. The pins are inserted into receiving aperture in the foot rest surface. Other ways are known in the art for providing this adjustable height feature such as a sliding mechanism in slots with tightening screws but for most cases, the preferred method described herein using pins is very economical and easy to use and in most cases will accommodate most foot sizes without having to resort to more complex system.

The tray or work station platform offers easy access to pedicure tools and supplies. The tray is also designed to provide secure placement of the polish bottles using partitioned compartments and a perimeter rim.

The pedestal folds to a narrow profile similar to a folding step stool for easy storage.

The invention further helps to protect home furnishings (kitchen and dining room tables, coffee tables, chairs, floors and rugs) from possible damage from tools, polish, or polish remover while providing a convenient and comfortable place for a do-it-yourself pedicure.

Operation of the Pedestal

To Open Pedestal for Use:

Spread pedestal legs apart.

Fold tray backward until the crossbar fits into one of the grooves on the back of the tray.

For the comfort of the person using the pedestal, several angles of the foot rest can be achieved by positioning the crossbar into each of the grooves on the back of the tray.

To Position the Pedestal for Use:

Position the opened pedestal with the foot rest facing where the person using the pedestal is seated.

Place the pedestal so that the foot that will be groomed rests comfortably in the middle of the foot rest. (The seating position of the user or the pedestal's position will be changed to accommodate comfortable placement of the other foot in the middle of the foot rest after grooming of the first foot is complete).

To Adjust the Toe Rest to Fit Foot Size:

Grasp the edges at each end of the toe rest and pull it evenly so that the two pins on the back of the toe rest pull smoothly out of holes in the foot rest.

Insert the pins in the foot rest holes that correspond with desired position for the toe rest.

Finer adjustments to the position of the rest can be made by turning the toe rest end over end and then placing it back on the foot rest. The pins in the toe rest may be located off-center so that when it is turned over, the toe rest can be finely adjusted in relation to a user's toe position on the foot rest.

The toe rest can be used to comfortably support either the toes or the ball of the foot being groomed.

To Return the Pedicure Pedestal to Its Folded Position for Storage:

After removing the pedicure tools and supplies from the work station platform, lift the back end of the tray to its upright position until it snaps into place between the side of the frame.

While lifting the pedestal lightly from the top of the frame, fold the legs of the frame together and the pedestal is ready for storage.

DETAILED DESCRIPTION OF THE INVENTION

Figure 1A:
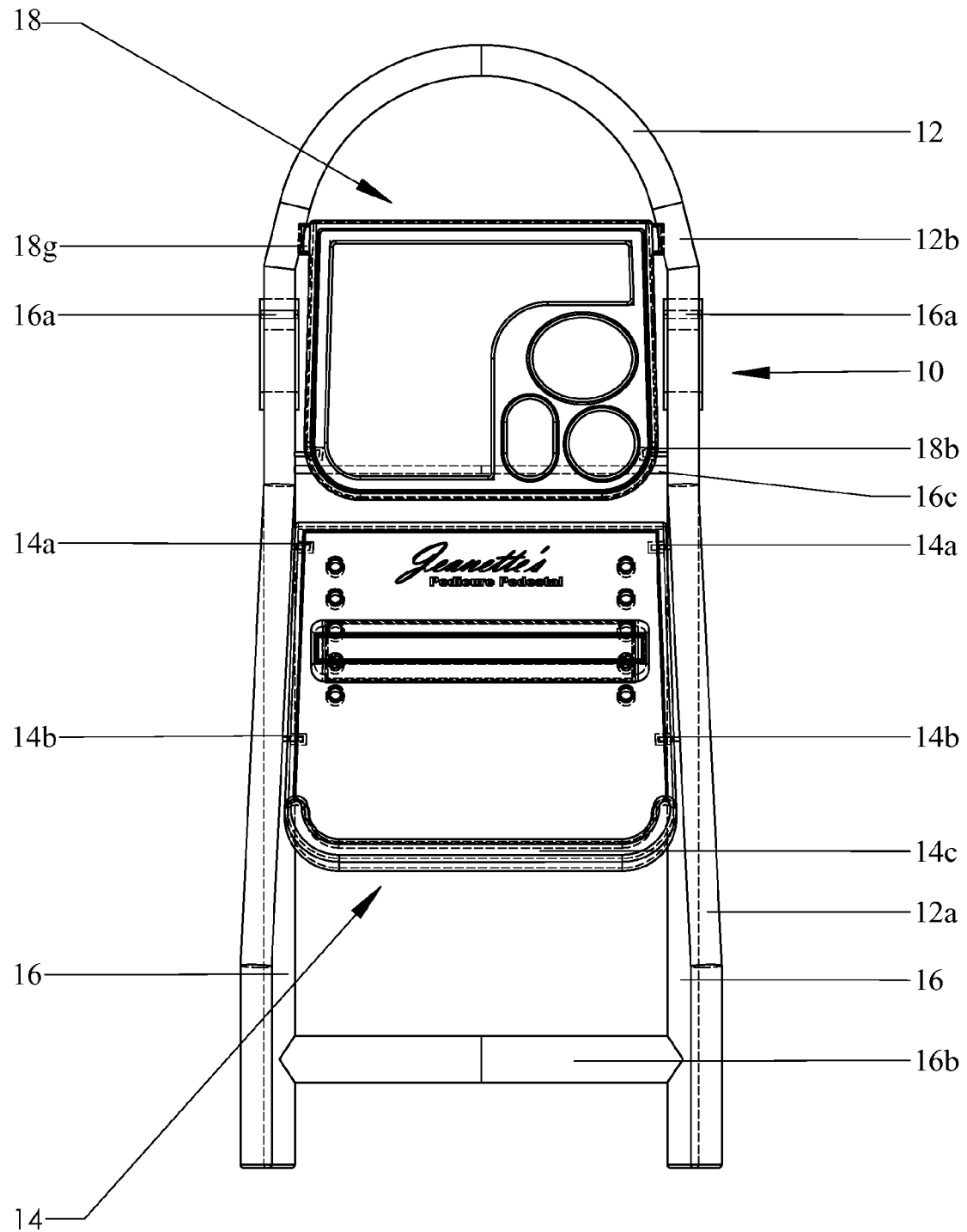
FIG. 1A is a frontal view of one embodiment of the present invention in a folded position.

Referring now to the drawings, FIGS. 1A-1E disclose one embodiment of the present invention, which is a pedicure pedestal assembly, depicted generally as 10.

Figure 1B:
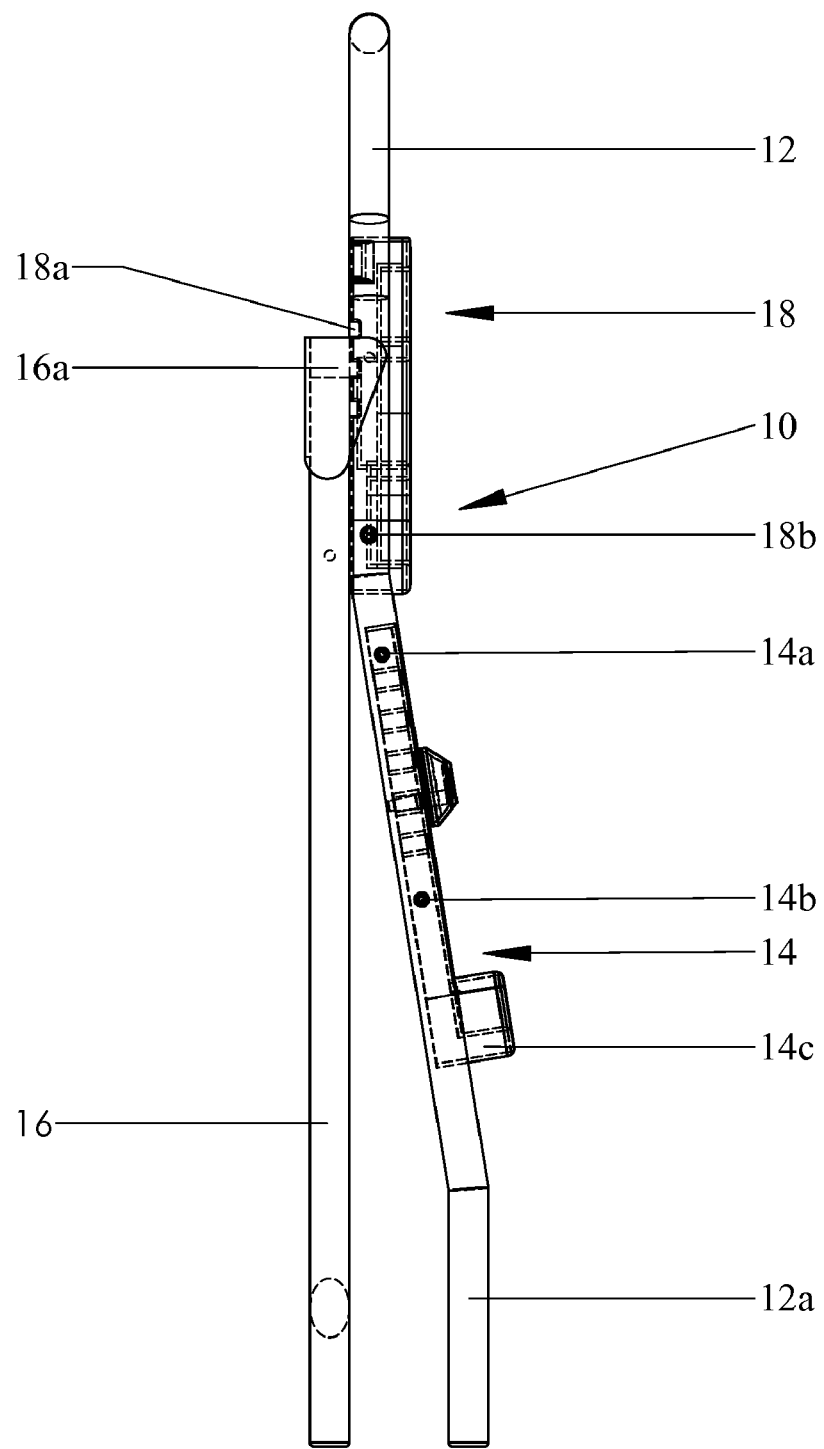
FIG. 1B is a side view of the embodiment of FIG. 1A.
Figure 1C:
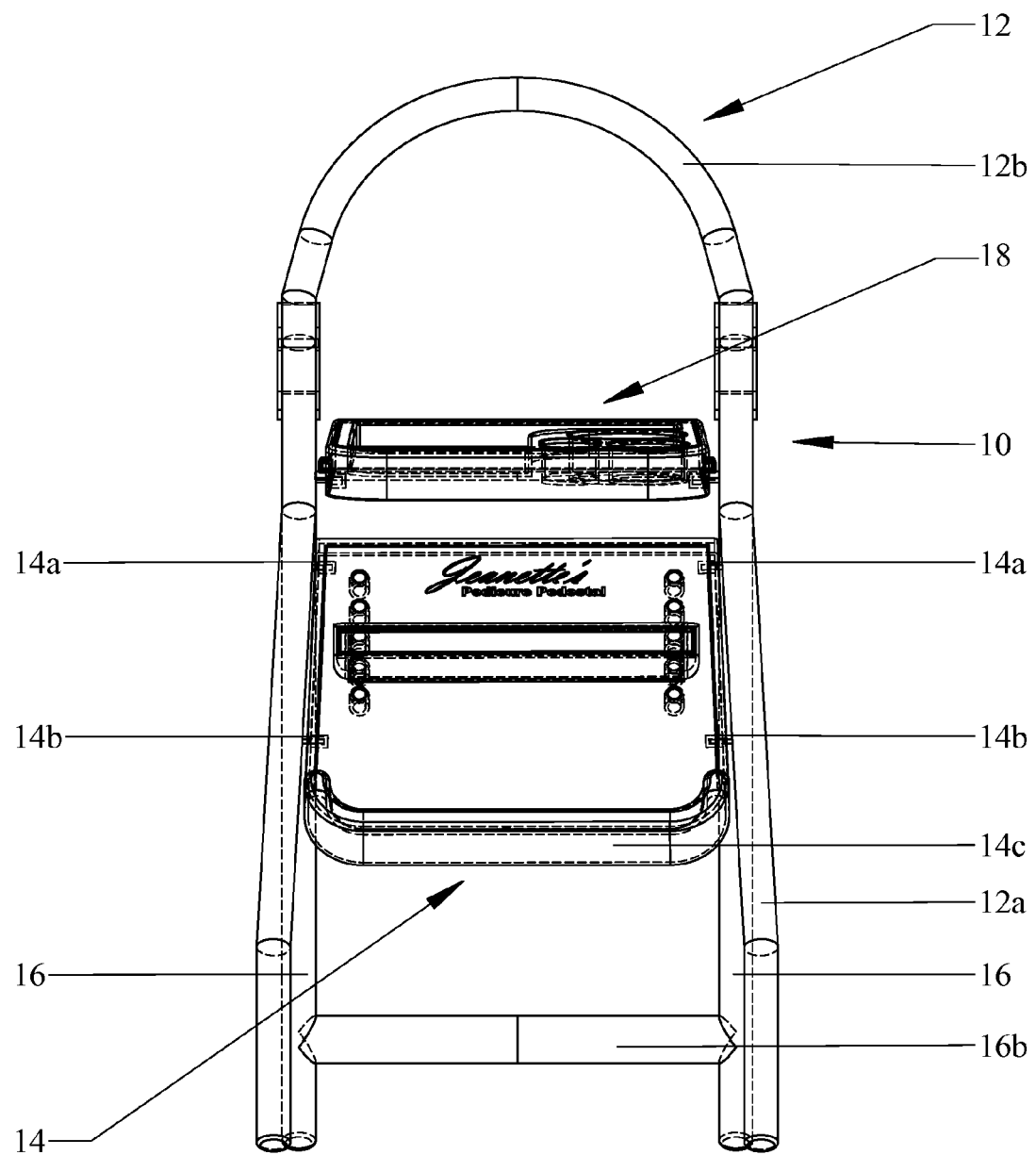
FIG. 1C is a frontal view of the embodiment of FIG. 1A in an open position.
Figure 1D:
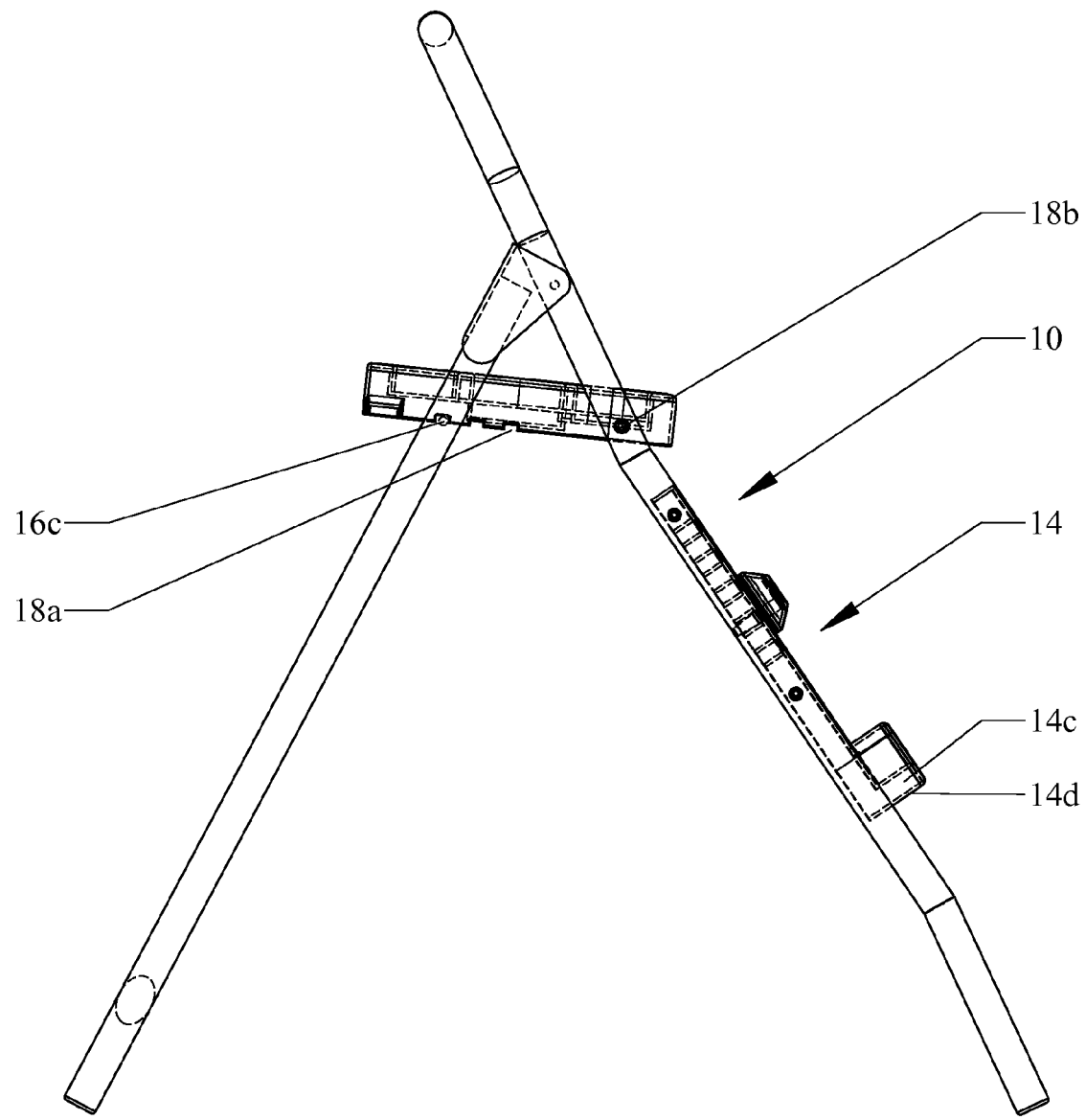
FIG. 1D is a side view of the embodiment of FIG. 1C.
Figure 1E:
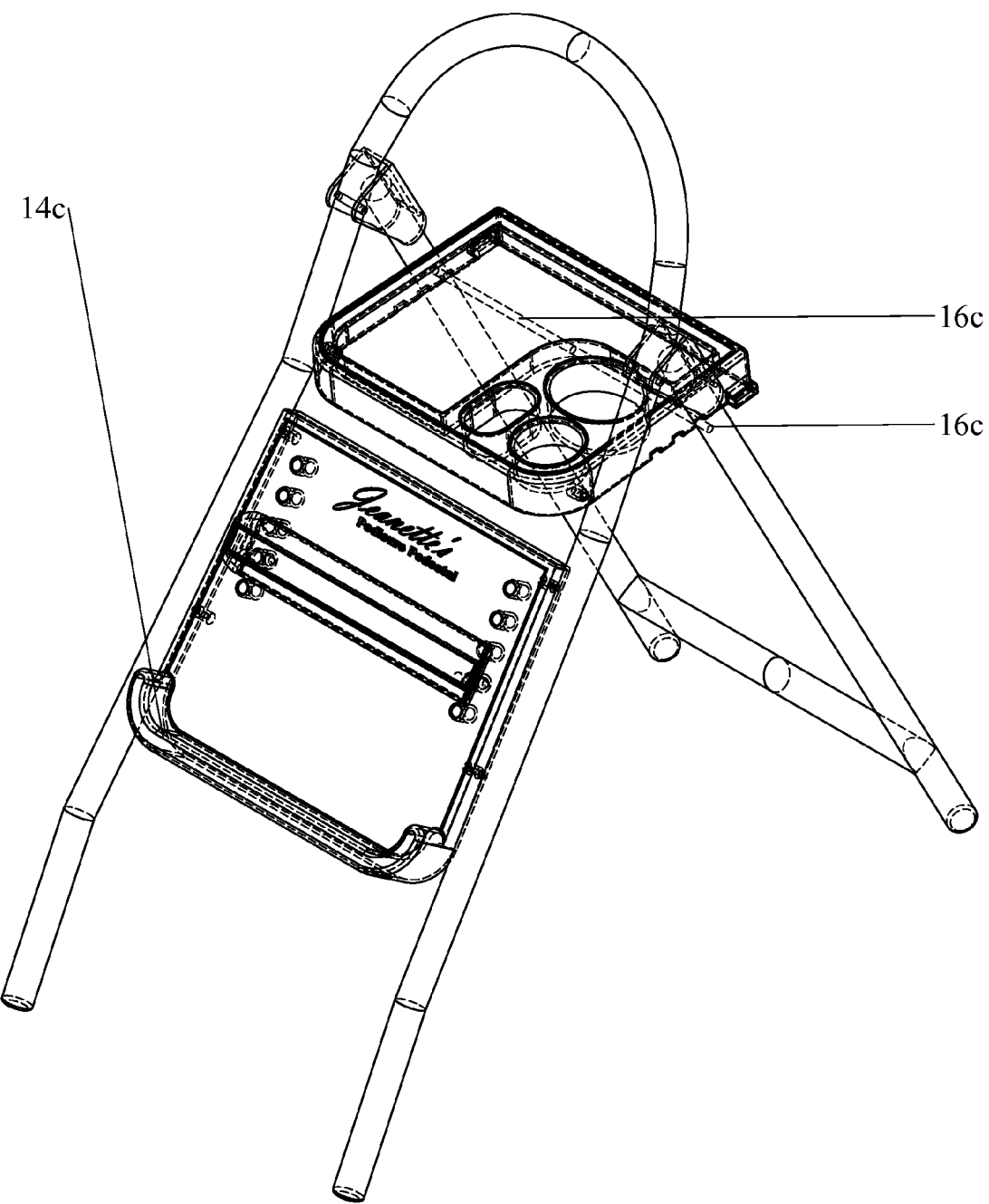
FIG. 1E is a perspective view of the embodiment of FIG. 1C.

The invention is a pedicure pedestal assembly 10, which includes a generally U-shaped frame member 12 having legs 12a of a predetermined length. As depicted in FIGS. 1A and 1B, the assembly 10 is in a folded position for storage. As depicted in FIG. 1C, the assembly 10 is in an open position for use. FIGS. 1A-1C show that the legs 12a are generally parallel to each other. The side view of FIG. 1B further shows that the legs 12a may be offset at a desired angle between a bottom portion of the legs 12a and an upper portion 12b of the U-shaped frame 12. The offset may be as desired to allow for the assembly 10 to free-stand when in closed position as in FIGS. 1A and 1B and also adds to the degree of incline for the footrest.

The assembly 10 also includes support member 14 located between the legs 12a of the U-shaped frame member 12 and attached thereto at an intermediate location of the legs 12a. As depicted, it is preferable that there be two attachment points 14a, 14b on each side of the foot support member 14. The preferred embodiments of the foot support member 14 will be further described below.

A pivotable frame member 16 is pivotably attached to the U-shaped frame member 12 at a location (see 16a pivot points) above the foot support member 14 so as to form a free-standing foldable pedestal frame assembly 10 when in an open position. The frame member 16 typically has a cross member 16b at its lower end and includes a hinge-like attachment at the top of the frame 16 parallel legs with a hinge pin, which serves as means for collapsing/folding or unfolding the assembly 10. There are several ways known in the art to configure the assembly 10 frame members 12, 16 to allow for this stability and that depicted is only by way of example.

The invention 10 further includes a work station platform 18 pivotably attached on each side to the legs 12a between the foot support member 14 and the pivotable frame attachment point 16a. The platform 18 is for example, pivotably attached as depicted at 18b. When the assembly 10 is in a closed position, the platform 18 has appendages 18c on each side of a distal side of the platform 18 that allows the platform 18 to rest against a part of the upper end of the U-shaped frame 12 as depicted in FIG. 1A.

Underneath a back or distal end or side of work station platform 18, spaced-apart parallel notches 18a are provided for adjustable engagement with a transverse member 16c extending between the pivotable frame member 16 such that when the pedestal frame assembly 10 is opened, the work station platform 18 is oriented in a generally horizontal orientation ready for holding tools and supplies for the pedicure and when the pedestal frame assembly 10 is in a closed position, the work station platform 18 is oriented in a generally vertical orientation for compactness and ease of storage. Other means near a distal end of work station platform for adjustably engaging the transverse member may be provided such as notches on the back side edge of the platform or retractable pins (serve as transverse member) and multiple hole connection means, slotted slide mechanism (pins that slides serve as transverse member), or other engagement means not shown in the drawings but known in the art. The drawings merely show one preferred method of engagement means.

Figure 4:
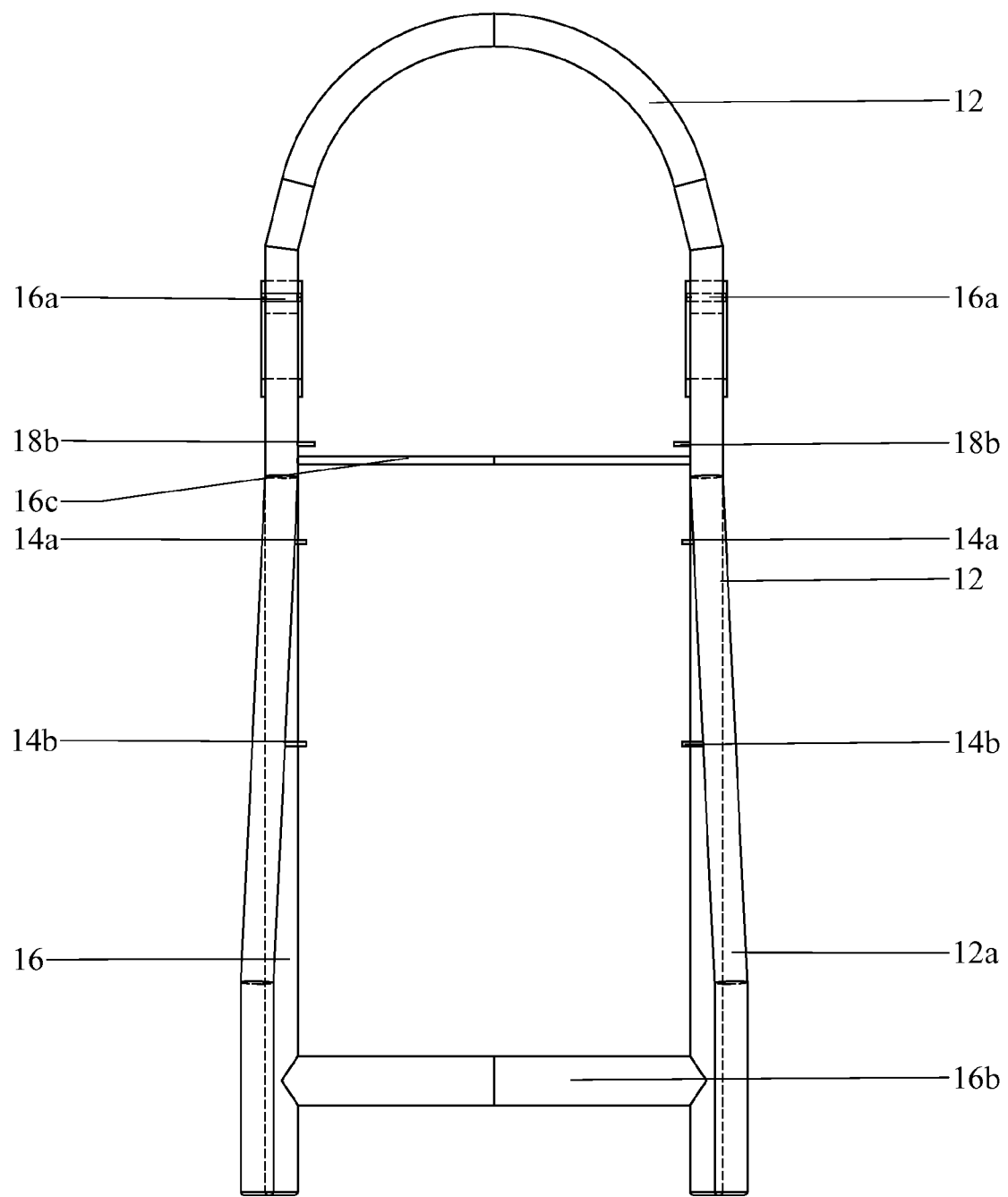
FIG. 4 is a frontal view of the pedestal frame system without the work station platform and the foot rest support.

FIG. 4 depicts the frame system 12, 16 without the foot support member 14 and the work station platform 18 for clarity as to the structure of the frame system 12, 16.

Figure 3A:
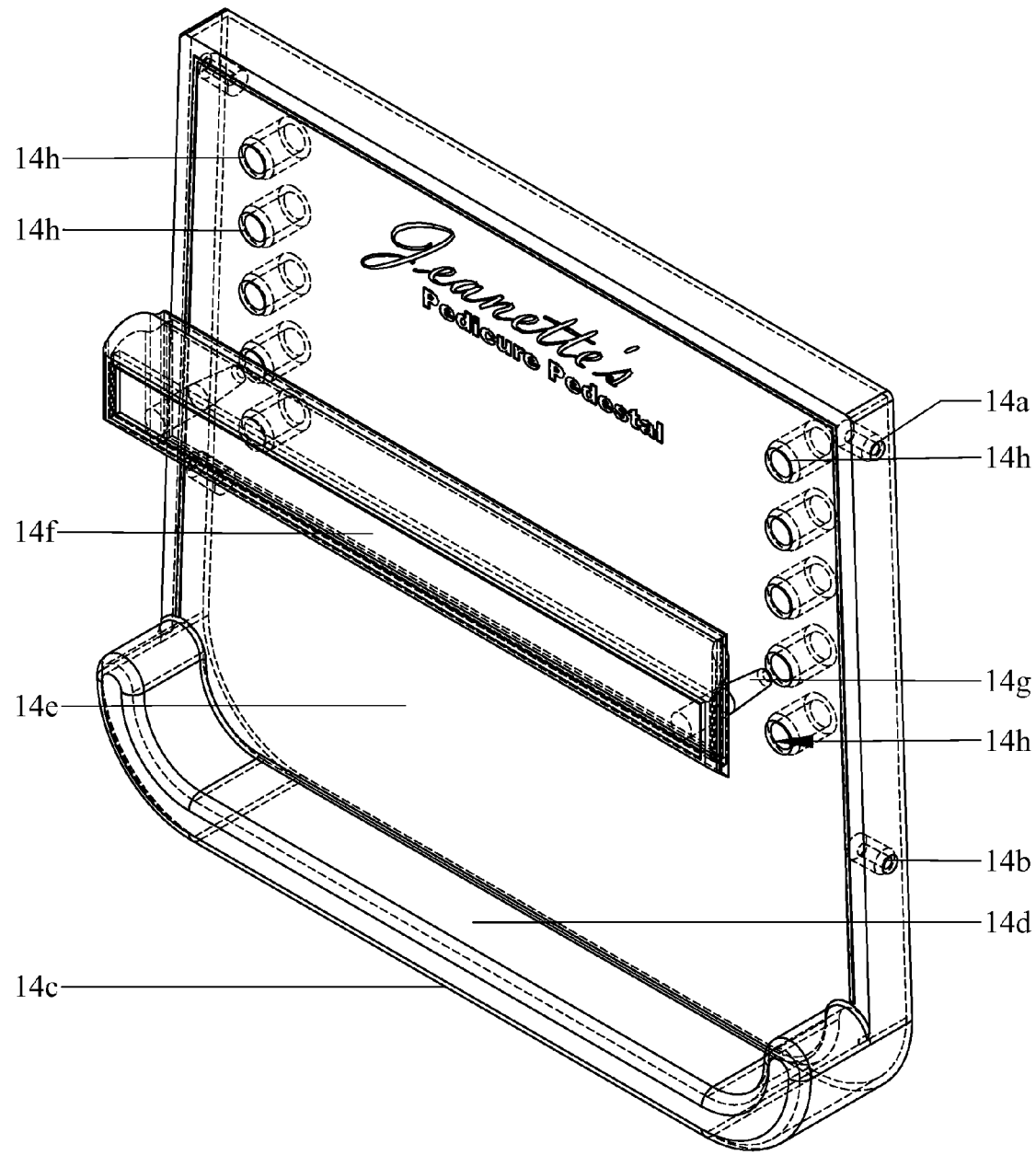
FIG. 3A is a perspective view of an example of a foot rest support.
Figure 3B:
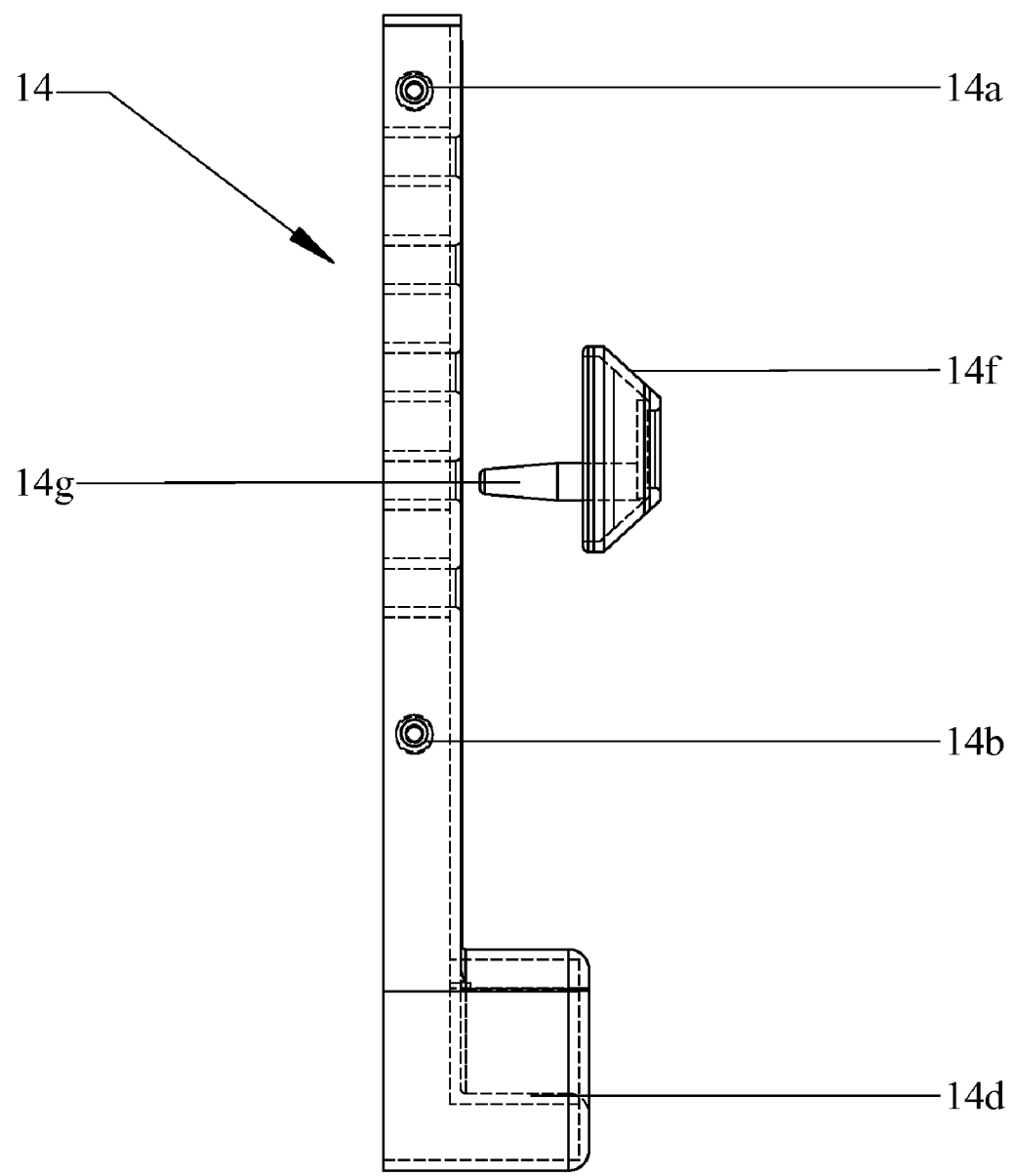
FIG. 3B is a side view of the FIG. 3A depiction.
Figure 3C:
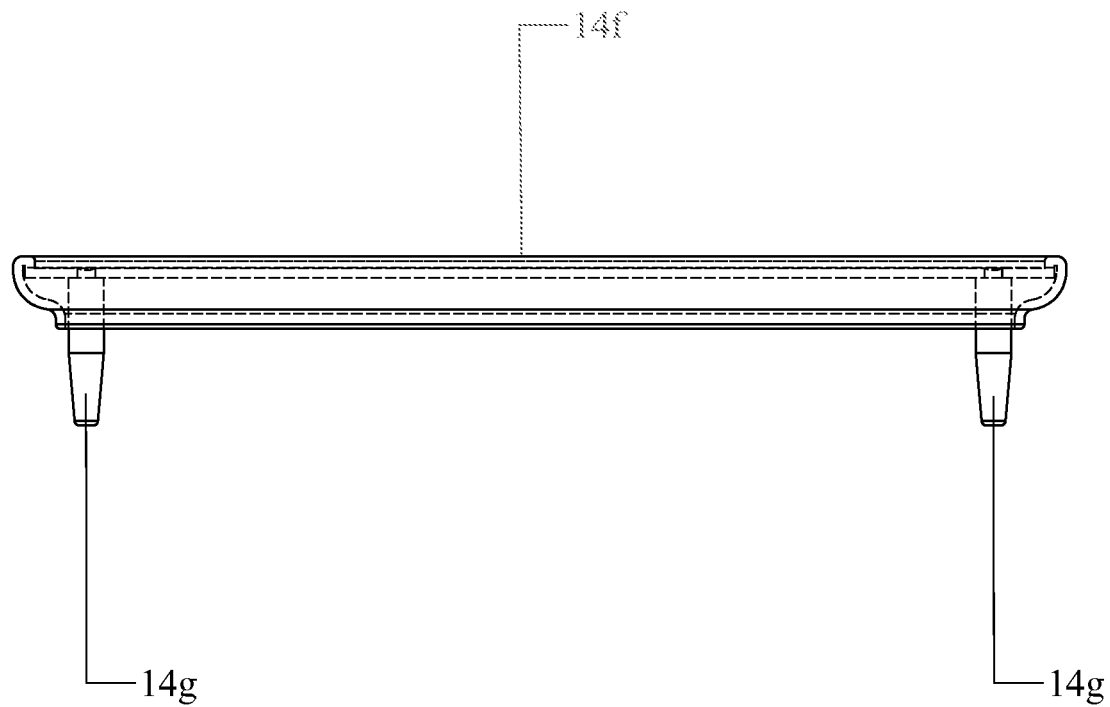
FIG. 3C is a side view of an example of a toe rest as depicted in FIGS. 3A-3B.

As further shown in FIGS. 3A-3C, the foot support member 14 preferably includes a heel rest support member 14c at the lower portion of the foot support member 14. Typically this heel rest 14c is an elevated member 14d extending generally perpendicular from a planar portion or surface 14e of the foot support member 14. This extended elevated member 14d is preferably at a height along the bottom edge of the support member 14 sufficient to support the back of a person's heel. For example, the extended height for heel support may be about ¾ of inch to about 1¼ inch in height. Optionally, this extended elevated member may also continue around the bottom respective corners somewhat as depicted in drawings.

The foot support member 14 also preferably includes a toe rest member 14f. The toe rest member is typically transversely oriented across the foot support member 14. It typically has a width of about 2 inches wide and length of about 12 inches wide, with a depth or thickness of about ¾ of an inch to about 1 inch. Optionally, padding (not shown) may be provided as desired to the toe rest surface and the heel support to provide for additional cushioning and comfort.

The foot support member 14 preferably includes means for adjusting a height of the toe rest member 14f from the heel rest support member 14c. One example of providing for this height adjustment features is to provide for a pair of spaced-apart pins 14g extending from a back side of the toe rest member 14f and a plurality of vertically oriented spaced-apart apertures 14h within the foot support member planar surface 14e, where the apertures 14h are spaced-apart and aligned so as to receive the pins 14g. As depicted in FIGS. 3A-3C, the toe rest 14f can be raised or lowered to accommodate the length of a person's foot so that when the person's heel is placed on the heel support 14c, the toe rest can be placed so the person's toes are located so as to facilitate the pedicure. As shown in FIG. 3B, in one embodiment, the pins 14g may be aligned in an off-center or offset alignment. This would allow a user to turn over or flip the toe rest 14f over to provide for a finer adjustment of the toe rest 14f in relation to a user's foot.

Figure 2A:
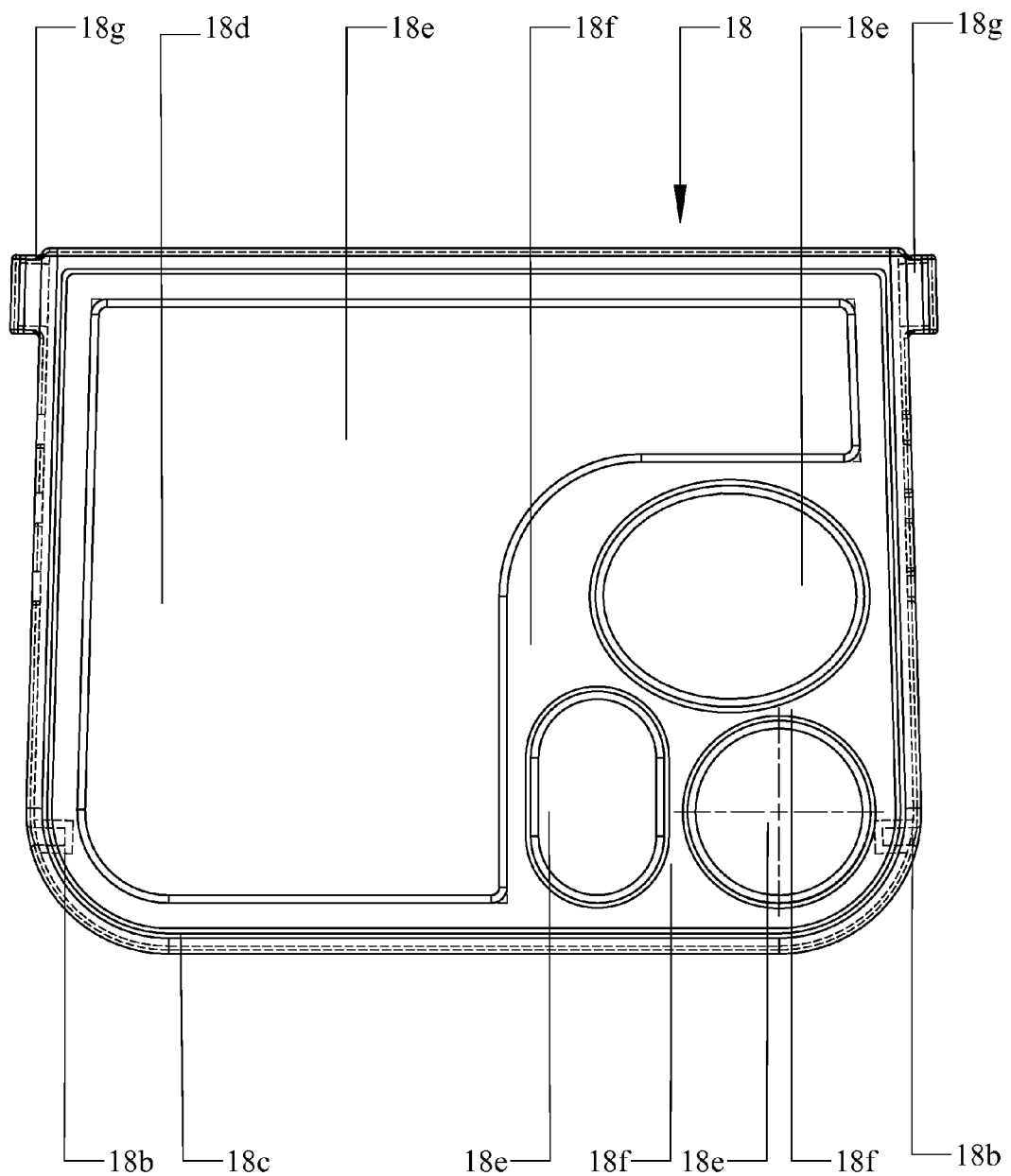
FIG. 2A is a plan view of an example of a work station platform.
Figure 2B:
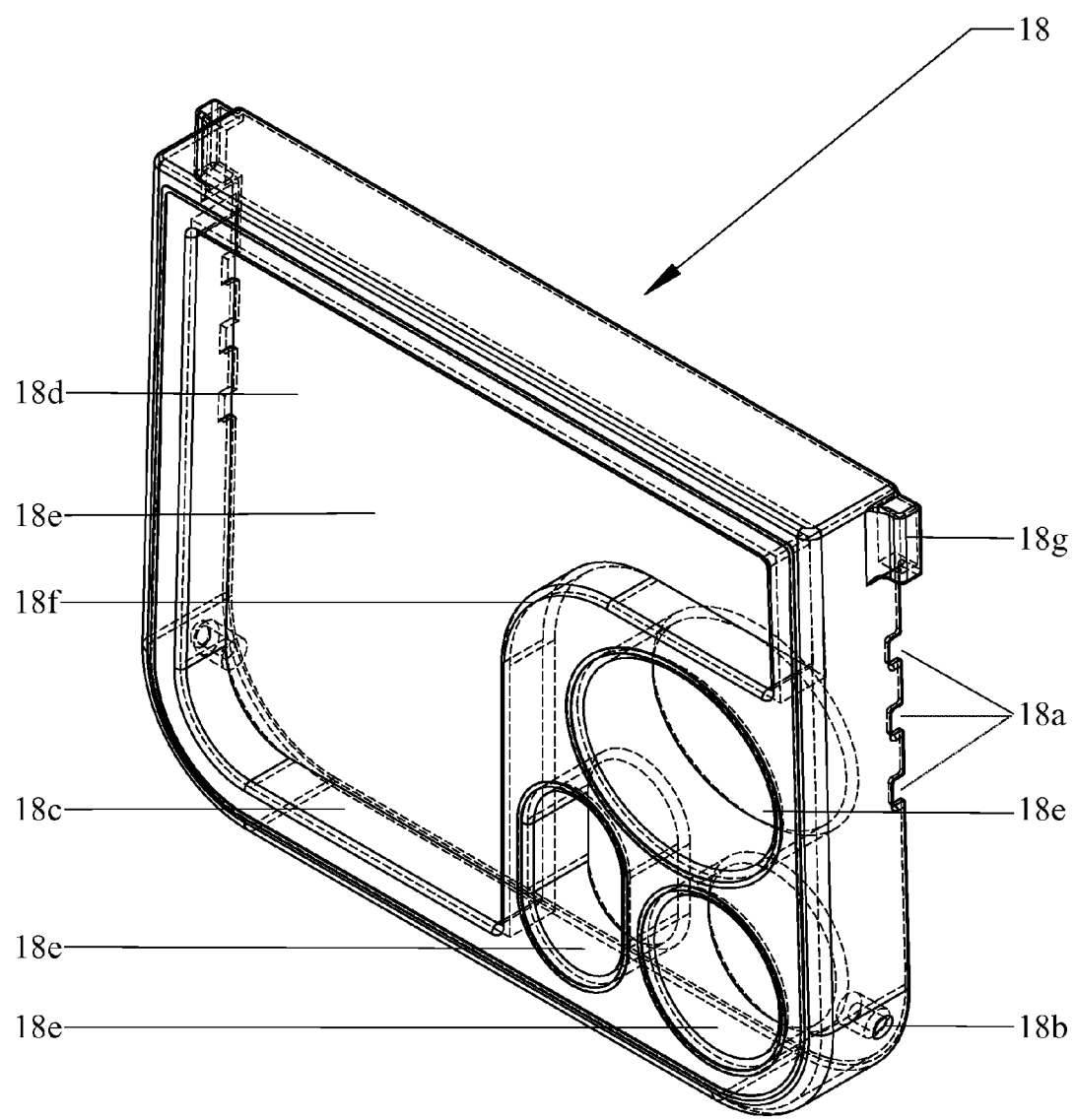
FIG. 2B is a perspective view of the platform embodiment of FIG. 2A.

As shown in FIGS. 2A-2B, the work station platform 18 preferably has an elevated portion 18c around a perimeter of the work station platform 18 preferably has an elevated portion 18c around a perimeter of the work station platform 18. The elevated portion 18c extends above a bottom surface 18d of the work station platform 18 at a height of about ¾ of an inch to about 1¼ inch from the bottom surface 18d. This platform 18 serves as a table or tray to hold the pedicure tools and supplies (not shown). In a preferred embodiment, the platform 18 also includes partioned sections to segregate tools and supplies. In this case, the platform 18 includes two or more partitioned sections or compartments or portions 18e within the perimeter elevated portion 18c of the work station platform 18. The partitioned portions 18e are formed by elevated portions 18f separating or forming each partitioned portion 18e. In the depiction, an example is provided of one general compartment or section for the working pedicure tools and three sections for holding various pedicure supplies. In FIG. 2A, appendages 18g are also provided at a distal end of the platform 18 to ensure that the platform 18 does not rotate and fall clockwise about pivot point 18b when folded as in FIG. 1B. The partition portions 18e may optionally include fingered collars (not shown) for snuggly holding polish bottles similar to those often incorporated in cup holders.

It is understood that the invention and its components can be made from a variety of materials known in the art. For example, the frame components may be made from generally light weight materials such as aluminum or other metallic materials or composite plastic or polymer based materials while the fool support and the work station platform can be made from metallic material, wood material, or composite plastic or polymer materials.

It should be understood that the preceding is merely a detailed description of one or more embodiments of this investigation and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed is:

1. A pedicure pedestal assembly comprising:
   a generally U-shaped frame member having legs of a predetermined length;
   a foot placement member comprising a non-pivotable pedicure working surface located between said legs of the U-shaped frame member and attached thereto at an intermediate location of said legs, said foot placement member being fixed to and parallel to said U-shaped frame member legs wherein when said pedicure pedestal assembly is opened for use, said pedicure working surface remains in a generally vertical orientation aligned with said U-shaped frame member legs;

a pivotable frame member pivotably attached to said U-shaped frame member at a location above said foot placement member so as to form a free-standing foldable pedestal frame assembly when in an open position; and a work station platform pivotably attached on each side to said legs between said foot placement member and said pivotable frame attachment, said work station platform having means near a distal end of said work station platform for adjustably engaging a transverse member attached to said pivotable frame member such that when said pedestal frame assembly is opened, said work station platform is oriented in a generally horizontal orientation and when said pedestal frame assembly is in a closed position, said work station platform is oriented in a generally vertical orientation.

2. The pedicure pedestal assembly according to claim 1, wherein the pedicure working surface comprises:
a heel rest member at a lower portion of said pedicure working surface.

3. The pedicure pedestal assembly according to claim 2, wherein said heel rest member is an elevated member extending generally perpendicular from a planar portion of said pedicure working surface at said lower portion of said pedicure working surface.

4. The pedicure pedestal assembly according to claim 1, wherein the pedicure working surface further comprises:
a toe rest member, said toe rest member being transversely oriented across said pedicure working surface.

5. The pedicure pedestal assembly according to claim 4, further comprising:
means for adjusting a height of said toe rest member from said heel rest member on said pedicure working surface.

6. The pedicure pedestal assembly according to claim 5, wherein said means for adjusting said height of said toe rest member from said heel rest member on said pedicure working surface comprises:
a pair of spaced-apart pins extending from a back side of said toe rest member and a plurality of vertically oriented spaced-apart apertures on said pedicure working surface, said apertures being spaced-apart and aligned so as to receive said pins.

7. The pedicure pedestal assembly according to claim 1, wherein said work station platform comprises:
an elevated portion around a perimeter of said work station platform, said elevated portion extending above a bottom surface of said work station platform.

8. The pedicure pedestal assembly according to claim 7, wherein said work station platform further comprises:
two or more partitioned sections within said perimeter elevated portion of said work station platform, said partitioned sections being formed by elevated portions separating each partitioned section, said separating elevated portions extending above said bottom surface of said work station platform.

9. The pedicure pedestal assembly according to claim 6, wherein said spaced-apart pins are located in an off-center alignment on said back side of said toe rest.

10. A pedicure pedestal assembly comprising:
a generally U-shaped frame member having legs of a predetermined length;

a foot placement member located between said legs of the U-shaped frame member and attached thereto at an intermediate location of said legs, wherein the foot placement member further comprises a toe rest member, said toe rest member being transversely oriented across said foot placement member;

a pivotable frame member pivotably attached to said U-shaped frame member at a location above said foot placement member so as to form a free-standing foldable pedestal frame assembly when in an open position;

a work station platform pivotably attached on each side to said legs between said foot placement member and said pivotable frame attachment, said work station platform having means near a distal end of said work station platform for adjustably engaging a transverse member attached to said pivotable frame member such that when said pedestal frame assembly is opened, said work station platform is oriented in a generally horizontal orientation and when said pedestal frame assembly is in a closed position, said work station platform is oriented in a generally vertical orientation; and means for adjusting a height of said toe rest member from said heel rest support member on said foot placement member, wherein said means for adjusting said height of said toe rest member from said heel rest support member on said foot placement member comprises:

a pair of spaced-apart pins extending from a back side of said toe rest member and a plurality of vertically oriented spaced-apart apertures on said foot placement member, said apertures being spaced-apart and aligned so as to receive said pins.

11. The pedicure pedestal assembly according to claim 10, wherein the foot placement member comprises:
a heel rest support member at a lower portion of said foot placement member.

12. The pedicure pedestal assembly according to claim 11, wherein said heel rest support member is an elevated member extending generally perpendicular from a planar portion of said foot placement member at said lower portion of said foot placement member.

13. The pedicure pedestal assembly according to claim 10, wherein said work station platform comprises:
an elevated portion around a perimeter of said work station platform, said elevated portion extending above a bottom surface of said work station platform.

14. The pedicure pedestal assembly according to claim 13, wherein said work station platform further comprises:
two or more partitioned sections within said perimeter elevated portion of said work station platform, said partitioned sections being formed by elevated portions separating each partitioned section, said separating elevated portions extending above said bottom surface of said work station platform.

15. The pedicure pedestal assembly according to claim 10, wherein said spaced-apart pins are located in an off-center alignment on said back side of said toe rest.

* * * * *